United States Patent [19]
Marshall

[11] 4,079,516
[45] Mar. 21, 1978

[54] APPARATUS FOR PREVENTING MERCURY CONTAMINATION

[75] Inventor: Thomas Donald Marshall, Clear Lake City, Tex.

[73] Assignee: Odyssey Corporation for Research and Development, Houston, Tex.

[21] Appl. No.: 701,501

[22] Filed: Jul. 1, 1976

[51] Int. Cl.² .............................................. A61C 3/00
[52] U.S. Cl. .................................................... 32/40 A
[58] Field of Search .............. 259/DIG. 22; 32/40 R, 32/40 A; 210/350, 351; 209/48, 56, 1, 2, 67, 69

[56] References Cited
U.S. PATENT DOCUMENTS

| | | | |
|---|---|---|---|
| 836,001 | 11/1906 | Argue | 32/40 A |
| 2,625,893 | 1/1953 | Semple | 32/40 A |
| 3,753,499 | 8/1973 | Gwilliam | 210/350 |

Primary Examiner—Robert Peshock
Attorney, Agent, or Firm—Arthur M. Dula; Murray Robinson; Ned L. Conley

[57] ABSTRACT

The invention is an apparatus for preventing mercury contamination during such processes as removing excess mercury from dental silver amalgam, mulling dental silver amalgam, and loading dental silver amalgam into a dispenser. The apparatus comprises a material permeable by free mercury under pressure and impermeable by dental silver amalgam. One surface of this material is enclosed by a flexible covering impermeable by either free mercury or mercury vapor. One or more voids are provided between the material and the covering for the purpose of retaining any excess mercury squeezed through the cloth. Means for enhancing retention of mercury in the void or voids may be provided.

7 Claims, 7 Drawing Figures

APPARATUS FOR PREVENTING MERCURY CONTAMINATION

BACKGROUND OF THE INVENTION

1. Field of the Invention

The present invention generally relates to dental tools and equipment and more particularly to a device for removing excess mercury from dental silver amalgam and/or for mulling dental silver amalgam. Still more particularly, the present invention relates to a device that minimizes exposure to liquid and gaseous mercury by eliminating mercury contact with skin during squeezing and/or mulling and by retaining excess mercury within a sealed, properly disposable system.

2. Background of the Prior Art

Dental silver amalgam is a dental restorative material used to fill cavities in teeth. In preparing dental silver amalgam, dentist or dental assistant mixes mercury with another metal, referred to as alloy, such as silver, copper, tin and zinc. Freshly mixed, dental silver amalgam has sufficient plasticity to be condensed into a prepared cavity.

The ratio of portions of mercury to alloy mixed together vary, but basically these ratios fall into two categories. The minimal mercury to alloy ratio has essentially equal portions of mercury and alloy. When fully mixed such that each particle of alloy is coated with mercury, amalgam mixed from this ratio may be applied to cavity without further processing. In the second category, portion of mercury is greater than portion of alloy resulting in an excess mercury to alloy ratio. This excess ratio facilitates the mixing process, but requires an additional processing step immediately after mixing: the excess mercury must be expressed from resultant amalgam prior to application.

Whether excess mercury or minimal mercury to alloy is used, dental silver amalgam must be mulled after mixing. Mulling generally involves squeezing bits of amalgam mass together into a larger mass so that it can be inserted either into a dispenser or directly into a cavity.

The oldest and most common method of expressing excess mercury and mulling is for the dentist to squeeze amalgam with his fingers. To remove excess mercury, the amalgam is wrapped in a cloth or similar filtering medium that is manually squeezed to expel excess mercury. Mulling may also be accomplished by squeezing amalgam while it is wrapped in a cloth, but a more common practice had been for the dentist to place the amalgam in the palm of one hand and knead it with the fingers of his other hand.

These techniques of squeezing and mulling amalgam create a danger of mercury poisoning as well as danger of contamination of amalgam with moisture from the fingers or hand of the operator or tray on which cloth is placed. Excess mercury squeezed through the cloth cannot be easily collected either for subsequent use or proper disposal. It is common practice for the dentists or dental assistants to shake excess mercury from the cloth. As a result, the mercury ends up on the dental tray, cabinet top, floor, and in clothing and shoes of personnel. Mercury is a liquid and will run between cracks in tile, under dentist's chairs and around other equipment where it collects over a period of time. This buildup of mercury in numerous inaccessible places can create a high concentration of mercury vapor that endangers the health of all persons working in the operatory. If the floor is swept or vacuumed, mercury is dispersed. This heightens mercury vapor concentration. Mercury deposited in a waste basket may ultimately be burned in an incinerator thus contaminating atmosphere; mercury washed away in waste water contributes to pollution of water. Additionally, both squeezing and mulling result in direct skin contact with mercury. Finally, these methods result in wasting a natural resource by failing to allow for a system for reprocessing unused excess mercury. Numerous articles have noted that the present methods of squeezing and mulling result in an increased risk of mercury poisoning to the dentist and his employees. Mantyla, *Protection of Dental Personnel Through Proper Mercury Hygiene,* DENTAL SURVEY (June 1973) 58, 60; Cedar, *Mercury Vapor: A Hazard in the Dentist's Office,* DENTAL STUDENT (February 1973) 28, 30; Buchwald, *Using Mercury Safely,* DENTAL HYGIENE (July-August 1973) 231, 234; Buchwald, *More About Mercury Hygiene,* 2.

The prior art teaches numerous devices developed for the purpose of retaining excess mercury squeezed from amalgam and for limiting contact between amalgam or mercury and skin to prevent contamination of the amalgam. Other devices have been developed for the express purpose of increasing efficiency in removing excess mercury and assuring higher quality amalgam, but these devices may also retain excess mercury and limit contact between mercury and skin. None of these devices, however, has been accepted commercially. A primary difficulty with these devices is that they are highly complex and costly. Examples of such highly complex devices may be found in U.S. Pat. Nos. 2,731,724, issued on the application of Nordeen (mechanically squeezes amalgam wrapped in cloth); 3,023,889, issued on the application of Barr (mixes amalgam in vibrator and centrifuges excess mercury from amalgam); 2,647,638, (vibrates excess mercury from amalgam through a screen in the end of a capsule). Other devices taught by the prior art force mercury from amalgam by operation of a plunger or plungers forced against the amalgam. Excess mercury may escape around the piston and into a reservoir, as in U.S. Pat. Nos. 3,065,543, issued on the application of McShirley, and 2,618,354, issued on the application of Lyon; or it may escape through a chamois skin against which amalgam is forced by a plunger, as in U.S. Pat. No. 2,212,116, issued on the application of Eberenz. Although plunger devices are less complex and costly than the previously discussed mechanical devices, they, too, have not been accepted in practical dentistry because they require additional time consuming steps; i.e., placing the amalgam in a small cylinder and then removing it. None of these devices provide a means for efficiently mulling amalgam. U.S. Pat. No. 2,716,816, issued on the application of Brown, teaches a device designed to minimize contact between skin and amalgam during mulling. While using the device, the dentist must wear a finger cot or the like. Furthermore, the device taught by Brown is not adapted to remove excess mercury from mulled amalgam. Because of these problems, manual manipulation remains essentially the exclusive method of removing excess mercury and mulling the amalgam.

Additionally, none of these prior art devices offer sufficient protection from mercury poisoning. Since all these devices require cleaning after use, there is a high probability of contamination of waste water. Devices requiring use of high speed amalgamators may contribute to mercury contamination by dissipating fine droplets of mercury through the air. See, Nixon and Rowbotham, *Mercury Hazards Associated with High Speed Mechanical Amalgamation,* 131 Brit. Dent. J. 308 (1971). Mercury contamination occurs during loading and unloading of the plunger devices and during the entire mulling process of the Brown, supra, device. It is clear therefore, in view of the health hazard imposed by regular exposure to mercury vapor, that there is a present need for a low-cost, safe, simple and easily utilized device that will allow removal of excess mercury from amalgam and mulling of amalgam during an operation while at the same time minimizing danger of mercury contamination.

It is an object of the present invention to provide a simple, low-cost device capable of mulling and removing excess mercury from amalgam while enhancing and promoting environmental protection by reducing contamination of air and water by mercury.

It is a further object of this invention to provide a device that will remove excess mercury from dental amalgam and mull amalgam during an operation that does not require the dentist to perform any tasks in addition to those presently practiced in the art.

It is a still further object of this invention to provide a device that eliminates direct skin contact with mercury or amalgam and permits direct loading of a dispenser.

It is yet still another object of this invention to promote conservation of mercury and amalgam scraps of silver, copper, tin and zinc.

It is yet a still further object of this invention to provide a device that prevents contamination of dental silver amalgam mass by moisture from fingers or hands of dentist or dental assistant, or by moisture from dental tray when device is placed on tray.

SUMMARY OF THE PRESENT INVENTION

The invention comprises a flexible material permeable by free mercury under pressure and impermeable by dental amalgam. One surface of the material is enclosed, at least in part, by a flexible covering impermeable by either free mercury or mercury vapor. One or more voids are provided between the material and the covering, such void or voids being completely enclosed by the material, the plastic, and a sealing means for sealing the covering to the material.

DESCRIPTION OF THE PREFERRED EMBODIMENT

Figure 1:
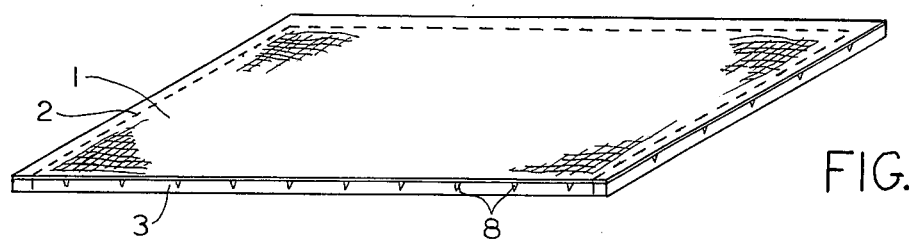
FIG. 1 is a sectional perspective drawing of the preferred embodiment when not in use.
Figure 2:
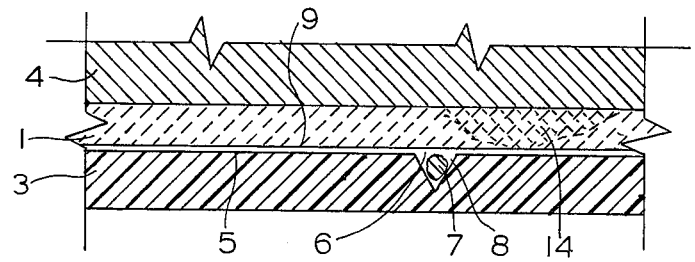
FIG. 2 is an enlarged sectional drawing of the preferred embodiment when in use with recesses of exaggerated enlargement.
Figure 5:
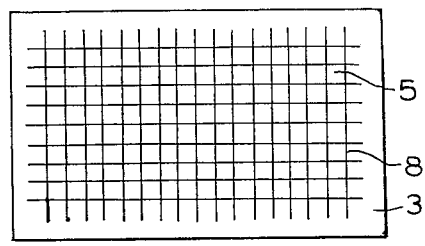
FIG. 5 is a plan view of the plastic sheet element of the preferred embodiment.

As seen in FIG. 1, flexible material 1 is juxtaposed to surface 5 of flexible plastic covering 3. In the preferred embodiment, material 1 and covering 3 are of the same size and shape and are secured together about their entire perimeter by seam 2. As seen in FIGS. 2 and 5, surface 5 of covering 3 is latticed with recessed areas 8. Surface 9 of material 1 and recessed areas 8 form cavities 6 wherein material 1 and sheet 3 do not come into contact.

Material 1 may be constructed from any material capable of passing excess mercury under pressure while retaining dental amalgam. Readily available materials are chamois skin and ordinary fabric. Material 1 can also be a piece of plastic having a plurality of apertures therethrough. Covering 3 may be constructed from any material capable of withstanding pressure used in squeezing amalgam without tearing. A readily available material that provides necessary durability and flexibility is mylar. Recesses 8 may be heatformed into mylar. Seam 2 must be adapted to both material 1 and covering 3 used in a particular embodiment. Seam 2 should not split during squeezing and mulling nor should it cause material 1 or covering 3 to tear at seam 2 during those operations. In the preferred embodiment, using chamois and mylar as material 1 and covering 3 respectively, a seam stitch commonly used in the art of sewing fabric to fabric may be used. This stitch should not be so fine as to cause covering 3 to tear easily at the seam. In the alternative, seam 2 may be an adhesive or a heat seal.

Figure 3:
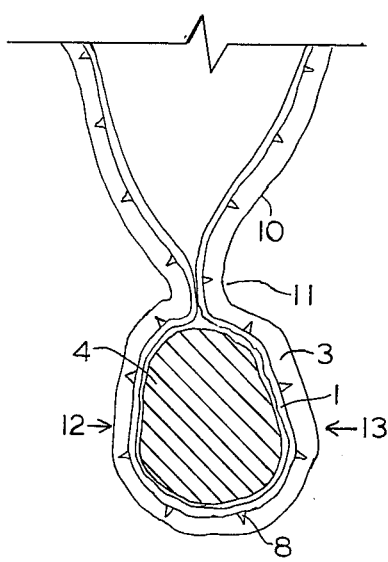
FIG. 3 is an enlarged sectional drawing of the preferred embodiment wrapped about an amalgam mass with recesses of exaggerated enlargement.
Figure 4:
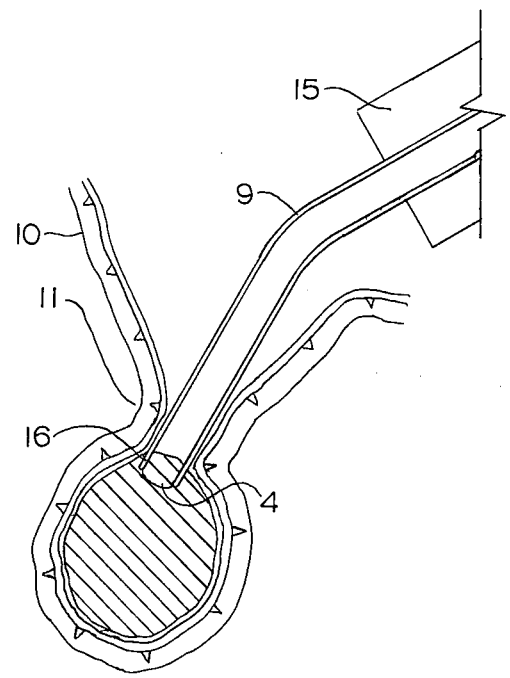
FIG. 4 is an enlarged sectional drawing of a dispenser being loaded directly from the preferred embodiment.

FIGS. 2 and 4 illustrate operation of apparatus. Whether removing excess mercury from amalgam or mulling dental silver amalgam, user deposits amalgam pellet 4 upon material 1 and entire apparatus is immediately wrapped about pellet 4 as in FIG. 3. Material 1 and covering 3 will extend about pellet 4 as at 10. Extension 10 should be twisted above pellet 4 so as to form neck 11 thus securing pellet 4 in a small pocket of material 1. Neck 11 formed by twisted extension 10 serves as a barrier to prevent escape of mercury vapor during squeezing and mulling operations.

With pellet 4 in place, user applies pressure with his fingers at 12 and 13 to perform operation. Such pressure forces mercury from pellet 4, through material 1 as at 14 in FIG. 2, and into cavity 6 as shown at 7. Squeezing is continued until all excess mercury has been removed or until amalgam has been mulled sufficiently.

FIG. 4 shows a method for inserting pellet 4 into a dispenser or syringe 15 with minimal exposure of mercury. By untwisting extension 10 and allowing neck 11 to open just enough to permit entry of tip 16 of tube 9 of dispenser 15, user can hold the entire apparatus in his or her palm, or rest it on a table top while holding neck closed about tip 16, and push tip 16 of tube 9 against pellet 4. This action forces pellet 4 into tube 9. The amalgam is then ready to be dispensed.

Figure 6:
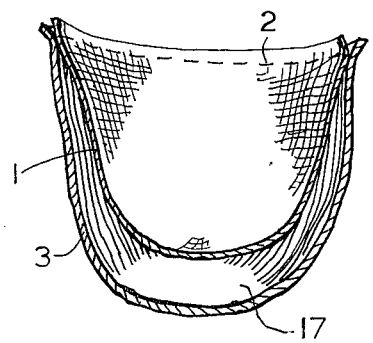
FIG. 6 is a sectional drawing of an alternative embodiment.

In the alternative embodiment of FIG. 6 the surface area of material 1 enclosed within seam 2 is less than the surface area of covering 3 enclosed within that same seam. As a result, gap or pocket 17 is provided between material 1 and covering 3. The operation of this alternative embodiment is substantially identical to that described for the preferred embodiment; but instead of being forced into the recesses as in the preferred embodiment, the excess mercury permeating the cloth may drop from the cloth and into pocket 17 where it is retained.

Figure 7:
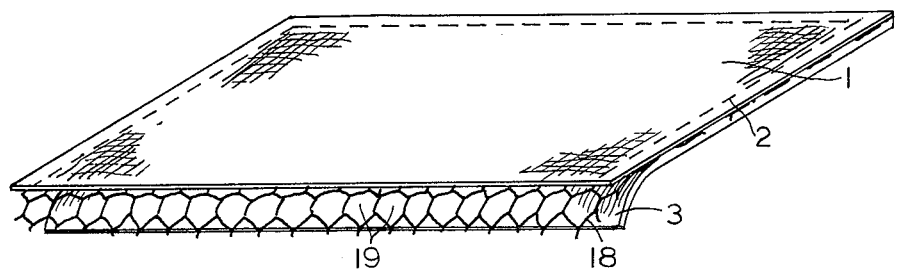
FIG. 7 is a sectional drawing of a second alternative embodiment with the major elements separated for illustrative purposes.

In the alternative embodiment of FIG. 7, the respective surface areas of material 1 and covering 3 within seam 2 are substantially the same. A mesh 18 is secured by seam 2 between material 1 and covering 3. Mesh 18 separates material 1 from covering 3 and provides voids 19 for retaining expressed mercury during the squeezing operation. The alternative embodiment may be combined with that of FIG. 6.

In yet another alternative embodiment, a mercury attractant substance may be substituted for mesh 18 of FIG. 7. Such a substance would be a thin flexible sheet of tin. Expressed mercury will amalgamate with tin thus further lessening mercury hazard.

When use of apparatus is complete, it is deposited in a sealed container for appropriate disposal. A used apparatus should not be combined with other trash that ultimately will be burned. A used apparatus could be delivered to a processor for recovering and recycling mercury and amalgam scraps trapped in the apparatus.

Apparatus of the present invention accomplishes function of removing excess mercury and mulling with the same success as the most commonly used device. The primary difference is that the apparatus of the present invention greatly reduces contamination resulting from contact with liquid and gaseous mercury. Mercury is trapped in an extremely small area and cannot be scattered throughout the office resulting in a very difficult and hazardous clean-up task.

While a preferred embodiment of the present invention has been shown and described, modifications thereof can be made by one skilled in the art without departing from the spirit of the present invention.

I claim:

1. Apparatus for mulling and squeezing excess mercury from dental amalgam comprising:
   a first piece of flexible material permeable by mercury and impermeable by dental amalgam, and
   a second piece of flexible material impermeable by liquid and gaseous mercury,
   a face of said first piece and a face of said second piece juxtaposed, and
   a securing means for attaching said first piece to said second piece,
   said first piece, said second piece and said securing means forming the bounds of at least one completely enclosed pocket,
   said face of said second piece having recesses.

2. Apparatus for mulling and squeezing excess mercury from dental amalgam according to claim 1 wherein said recesses are grooves formed in said face of said second piece.

3. Apparatus for mulling and squeezing excess mercury from dental amalgam according to claim 2 wherein said grooves form a lattice pattern on said face of said second piece.

4. Apparatus for mulling and removing excess mercury from dental amalgam comprising:
   a first piece of flexible material permeable by mercury and impermeable by dental amalgam, and
   a second piece of flexible material impermeable by liquid and gaseous mercury,
   at least a portion of a surface of said first piece covered by said second piece, and
   a securing means for attaching said second piece to said first piece, and
   a void completely enclosed by said first piece, said second piece and said securing means, said void including recesses in surface of said second piece facing said surface of said second piece.

5. Apparatus for mulling and removing excess mercury from dental amalgam comprising:
   a first piece of flexible material permeable by mercury and impermeable by dental amalgam, and
   a second piece of flexible material impermeable by liquid and gaseous mercury,
   at least a portion of a surface of said first piece covered by said second piece, and
   a securing means for attaching said second piece to said first piece, and
   a void completely enclosed by said first piece, said second piece and said securing means, said void including at least one mesh material secured between said first piece and said second piece.

6. Apparatus for mulling and removing excess mercury from dental amalgam comprising:
   a first piece of flexible material permeable by mercury and impermeable by dental amalgam, and
   a second piece of flexible material impermeable by liquid and gaseous mercury,
   at least a portion of a surface of said first piece covered by said second piece, and
   a securing means for attaching said second piece to said first piece, and
   a void completely enclosed by said first piece, said second piece and said securing means, said void including a mercury attractant substance disposed between said first piece and said second piece.

7. Apparatus according to claim 6 wherein said void further includes at least one mesh material secured between said first and said second piece.

UNITED STATES PATENT OFFICE
CERTIFICATE OF CORRECTION

Patent No. 4,079,516  Dated MARCH 21, 1978

Inventor(s) Thomas Donald Marshall

It is certified that error appears in the above-identified patent and that said Letters Patent are hereby corrected as shown below:

Column 2, line 30, change "difficult" to -- difficulty --.

Signed and Sealed this

Fifteenth Day of May 1979

[SEAL]

Attest:

RUTH C. MASON
Attesting Officer

DONALD W. BANNER
Commissioner of Patents and Trademarks